US012797553B2

(12) United States Patent
Moynihan

(10) Patent No.: US 12,797,553 B2
(45) Date of Patent: Nov. 17, 2026

(54) SAFETY APPARATUS FOR A MULTI-DOSE SYRINGE

(71) Applicant: Laurence Redmond Moynihan, Hull (GB)

(72) Inventor: Laurence Redmond Moynihan, Hull (GB)

( * ) Notice: Subject to any disclaimer, the term of this patent is extended or adjusted under 35 U.S.C. 154(b) by 861 days.

(21) Appl. No.: 18/303,830

(22) Filed: Apr. 20, 2023

(65) Prior Publication Data

US 2023/0338664 A1 Oct. 26, 2023

(30) Foreign Application Priority Data

Apr. 21, 2022 (GB) ...................................... 2205849

(51) Int. Cl.
*A61M 5/315* (2006.01)

(52) U.S. Cl.
CPC .... *A61M 5/31505* (2013.01); *A61M 5/31551* (2013.01); *A61M 5/3158* (2013.01)

(58) Field of Classification Search
CPC .......... A61M 5/31501; A61M 5/31505; A61M 5/31528; A61M 5/31536; A61M 5/3155; A61M 5/31563
See application file for complete search history.

(56) References Cited

U.S. PATENT DOCUMENTS

| | | | | |
|---|---|---|---|---|
| 2,551,902 A * | 5/1951 | Rieck | A61M 5/3202 | 604/173 |
| 3,128,765 A * | 4/1964 | Tint | A61M 5/31586 | 604/232 |

(Continued)

FOREIGN PATENT DOCUMENTS

| | | |
|---|---|---|
| CN | 202314751 U | 7/2012 |
| CN | 104162209 A | 11/2014 |

(Continued)

OTHER PUBLICATIONS

UKIPO Examination Report for GB2205849.9, Jun. 14, 2023 (6 pages).
EPO Extended European Search Report for EP23169136.1 (8 pages).

*Primary Examiner* — Gerald L Sung
(74) *Attorney, Agent, or Firm* — Koffsky Schwalb LLC; Mark I. Koffsky

(57) ABSTRACT

Safety apparatus (2) for a multi-dose syringe (4), wherein the multi-dose syringe (4) comprises:
(i) a syringe barrel (6);
(ii) a plunger (8) which operates in the syringe barrel (6);
(iii) a dose scale (10) on the syringe barrel (6);
(iv) screw threads (12) on the syringe barrel (6); and
(v) a dose dial (14) which screws along the screw threads (12) for dialling an injection dose on the dose scale (10);
wherein the safety apparatus (2) comprises:
(vi) a body (16) for extending along the syringe barrel (6);
(vii) a stopper member (18) which is at a first end portion (20) of the body (16) and which is for stopping depression of the plunger (8) in the syringe barrel (6); and
(viii) a locating member (22) which is at a second end portion (24) of the body (16) and which is for locating against the dose dial (14);
and wherein the safety apparatus (2) is such that:
(ix) the safety apparatus (2) is securable in position on the multi-dose syringe (4) by screwing the dose dial (14) along the screw threads (12) such that the dose dial (14) tightens against the locating member (22) and thereby causes the stopper member (18) to (Continued)

engage the plunger (8) such as to stop the depression of the plunger (8) into the syringe barrel (6) and thereby to stop injection of a dose from the multi-dose syringe (4).

8 Claims, 7 Drawing Sheets

(56) References Cited

U.S. PATENT DOCUMENTS 4,275,729 A * 6/1981 Silver ............... A61M 5/31551 604/211
4,475,905 A 10/1984 Himmelstrup
4,642,102 A * 2/1987 Ohmori ............... A61M 5/3158 604/220
4,946,441 A * 8/1990 Laderoute ............. A61J 1/1406 604/218
5,226,895 A * 7/1993 Harris ............... A61M 5/31591 604/218
5,876,380 A * 3/1999 Manganini .......... A61M 5/3158 604/88
7,611,495 B1 * 11/2009 Gianturco ........... A61M 5/3135 604/207
2007/0225656 A1 * 9/2007 Hoyle ................. A61M 5/2429 604/207
2013/0090603 A1 * 4/2013 Hoyle, Jr. ........... A61M 5/3158 604/189
2020/0306453 A1 10/2020 Langley
2021/0146058 A1 5/2021 Shetty et al.

FOREIGN PATENT DOCUMENTS

CN 213554474 U 6/2021
CN 113304377 A 8/2021
CN 215275097 U 12/2021
CN 215961569 U 3/2022
JP 2006026280 A1 2/2006
WO 9501198 A1 1/1995
WO 2015047758 A3 4/2015

* cited by examiner

SAFETY APPARATUS FOR A MULTI-DOSE SYRINGE

This invention relates to safety apparatus for a multi-dose syringe.

Multi-dose syringes are known for use in administering a required substance, for example a drug, for a patient. There is a possibility that the intended doses may be exceeded both in terms of volume and also frequency of administration. This is especially so if the multi-dose syringe is being used in a pre-hospital environment. In addition, the contents of a loaded multi-dose syringe may not be adequately protected when the multi-dose syringe is in transit.

It is an aim of the present invention to reduce the above mentioned problems.

Accordingly, in one non-limiting embodiment of the present invention there is provided safety apparatus for a multi-dose syringe, wherein the multi-dose syringe comprises:
- (i) a syringe barrel;
- (ii) a plunger which operates in the syringe barrel;
- (iii) a dose scale on the syringe barrel;
- (iv) screw threads on the syringe barrel; and
- (v) a dose dial which screws along the screw threads for dialling an injection dose on the dose scale;

wherein the safety apparatus comprises:
- (vi) a body for extending along the syringe barrel;
- (vii) a stopper member which is at a first end portion of the body and which is for stopping depression of the plunger in the syringe barrel; and
- (viii) a locating member which is at a second end portion of the body and which is for locating against the dose dial;

and wherein the safety apparatus is such that:
- (ix) the safety apparatus is securable in position on the multi-dose syringe by screwing the dose dial along the screw threads such that the dose dial tightens against the locating member and thereby causes the stopper member to engage the plunger such as to stop the depression of the plunger into the syringe barrel and thereby to stop injection of a dose from the multi-dose syringe.

The safety apparatus of the present invention is advantageous in that it is able to be used on the multi-dose syringe such as to stop the depression of the plunger into the syringe barrel and thereby stop injection of a dose from the multi-dose syringe.

Thus the safety apparatus is able to provide safety in that it has to be removed from the multi-dose syringe before the multi-dose syringe can be operated. This helps to concentrate the mind of an operator of the multi-dose syringe and thereby helps to avoid incorrect dialling of a dose and also injection time periods which are too frequent. Also, when the safety apparatus is on the multi-dose syringe, accidental depression of the plunger into the syringe barrel is able to be avoided and thereby the contents of the multi-dose syringe are able to be protected against unwanted loss.

The safety apparatus may be one in which the body is an elongate body. Other shapes for the body may be employed. When the body is an elongate body, then the elongate body may be in the form of a column. Other shapes for the elongate body may be employed.

The safety apparatus may be one in which the stopper member engages the multi-dose syringe by extending underneath an operator squeeze formation on the plunger. The stopper member may be configured to otherwise engage the multi-dose syringe in order to stop the depression of the plunger into the syringe barrel.

In all embodiments of the invention, the stopper member may be a lug formation which extends from the body such as to engage the plunger. Other formations for the stopper member may be employed.

The safety apparatus may be one in which the locating member is a wedge formation for becoming wedged in position between the dose dial and the outside of the syringe barrel. Other types of locating member may be employed.

When the locating member is a wedge formation, then the wedge formation may comprise a face portion for engaging with the outside of the syringe barrel, and a curved portion for engaging with the dose dial. Other shapes for the wedge formation may be employed.

The safety apparatus may include a guide formation for guiding the safety apparatus during the positioning the safety apparatus on the syringe barrel.

The guide formation may comprise two guide arms which extend from the body at an angle to each other such as to extend around a part of the outside of the syringe barrel. Other configurations for the guide formation may be employed.

The present invention also extends to the combination of the safety apparatus of the present invention and the multi-dose syringe.

Embodiments of the invention will now be described solely by way of example and with reference to the accompanying drawings in which.

Figure 1:
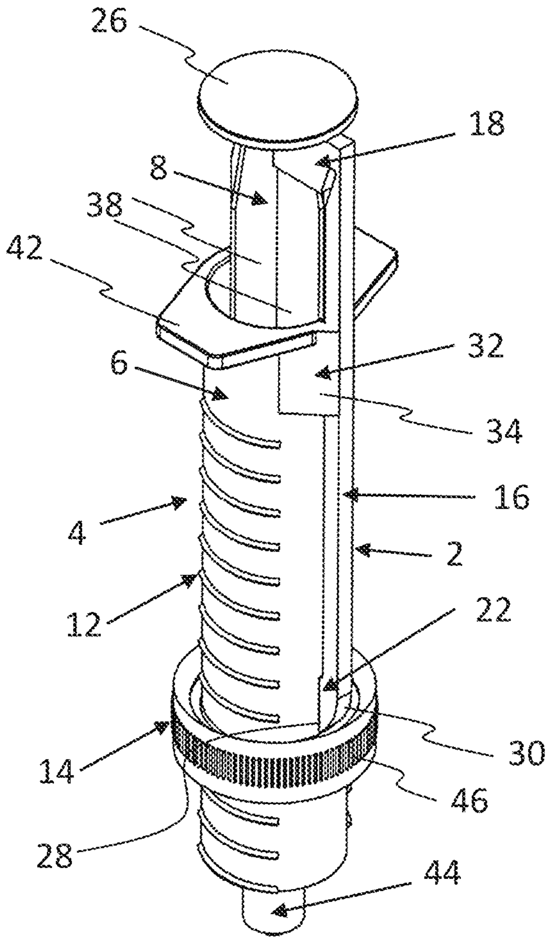
FIG. 1 is an isometric view of safety apparatus of the present invention on a multi-dose syringe.
Figure 2:
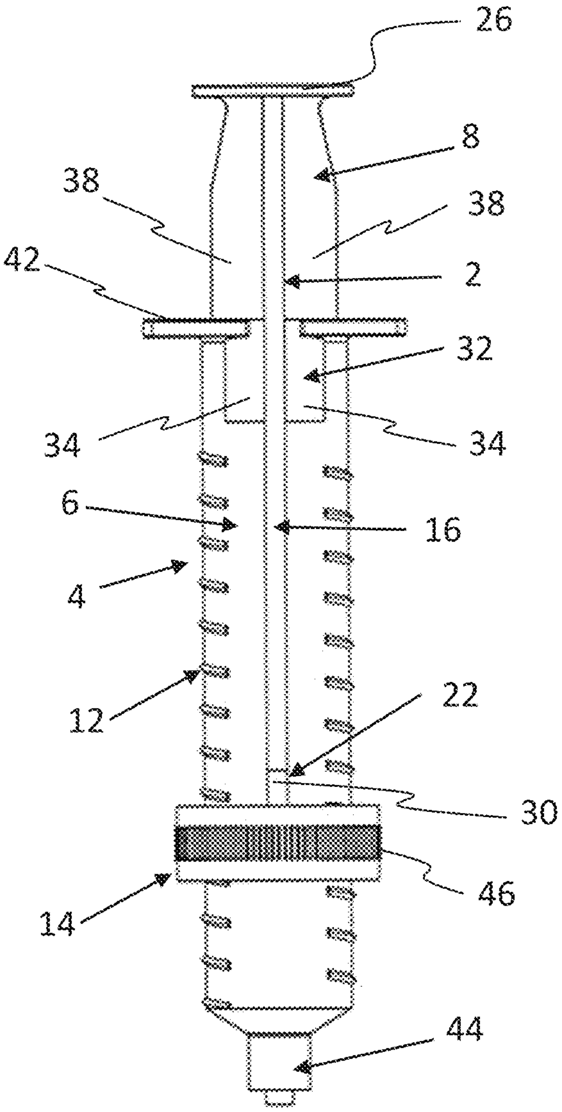
FIG. 2 is a front view of the safety apparatus and the multi-dose syringe as shown in FIG. 1.
Figure 3:
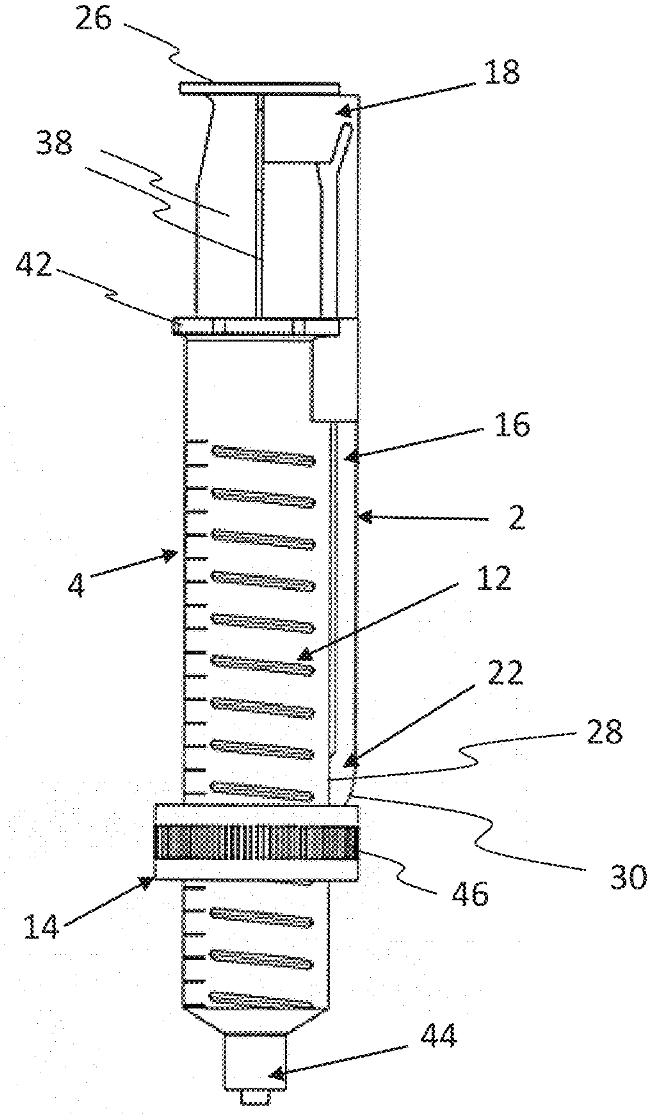
FIG. 3 is a side view from the left of the safety apparatus and the multi dose syringe as shown in FIG. 1.
Figure 4:
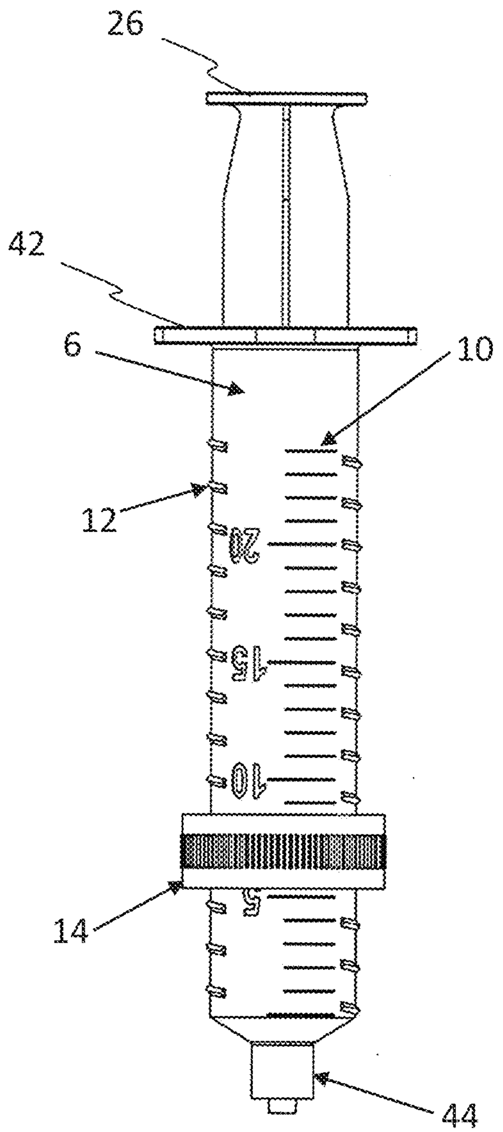
FIG. 4 is a rear view of the safety apparatus and the multi-dose syringe as shown in FIG. 1.

Referring to the drawings, there is shown safety apparatus 2 for a multi-dose syringe 4.

The multi-dose syringe 4 is a known multi-dose syringe and it comprises a syringe barrel 6 and a plunger 8 which operates in the syringe barrel 6. The syringe barrel 6 has a dose scale 10 on the syringe barrel 6. Screw threads 12 are also on the syringe barrel 6. The multi-dose syringe 4 also comprises a dose dial 14 which screws along the screw threads 12 for dialling an injection dose on the dose scale 10.

The safety apparatus 2 comprises a body 16 for extending along the syringe barrel 6. The safety apparatus 2 also comprises a stopper member 18 which is at a first end portion 20 of the body 16. The stopper member 18 is for stopping depression of the plunger 8 into the syringe barrel 6.

The safety apparatus 2 further comprises a locating member 22 which is at a second end portion 24 of the body 16. The locating member 22 is for locating against the dose dial 14.

The safety apparatus 2 is such that it is securable in position on the multi-dose syringe 4 by screwing the dose dial 14 along the screw threads 12 such that the dose dial 14 tightens against the locating member 22. This thereby causes the stopper member 18 to engage the plunger 8 such as to stop the depression of the plunger 8 into the syringe barrel 6 and thereby to stop injection of a dose from the multi-dose syringe 4.

The body 16 is an elongate body. More specifically, the elongate body is a column.

The stopper member 18 engages the multi-dose syringe 4 by extending underneath an operator squeeze formation 26 on the plunger 8. The operator squeeze formation 26 is in the form of a circular disc as can best be appreciated from FIG. 1.

The stopper member 18 is a lug formation which extends from the body 16 such as to engage the plunger 8. More specifically, the stopper member 18 extends underneath the operator squeeze formation 26 on the plunger 8.

The locating member 22 is a wedge formation for becoming wedged in position between the dose dial 14 and the outside of the syringe barrel 6. The locating member 22 in the form of the wedge formation comprises a face portion 28 for engaging with the outside of the syringe barrel 6, and a curved portion 30 for engaging with the dose dial 14. As can best be seen from FIG. 1, the curved portion 30 extends longitudinally along the second end portion 24 of the body 16 and curves towards the end of the body 16. The face portion 28 is a flat face portion and it is opposite the curved portion 30.

The safety apparatus 2 includes a guide formation 32 for guiding the safety apparatus 2 during the positioning of the safety apparatus 2 on the syringe barrel 6. The guide formation 32 comprises two guide arms 34, 36. The two guide arms 34, 36 extend from the body 16 at an angle to each other such as to extend around a part of the outside of the syringe barrel 6.

Figure 5:
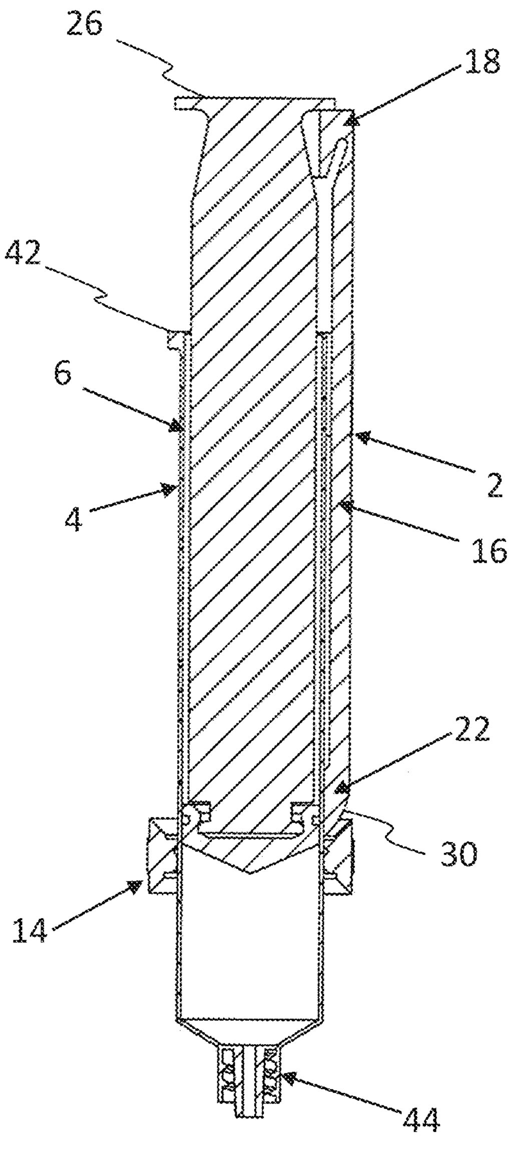
FIG. 5 is a longitudinal section through the line A-A shown in FIG. 1.
Figure 6:
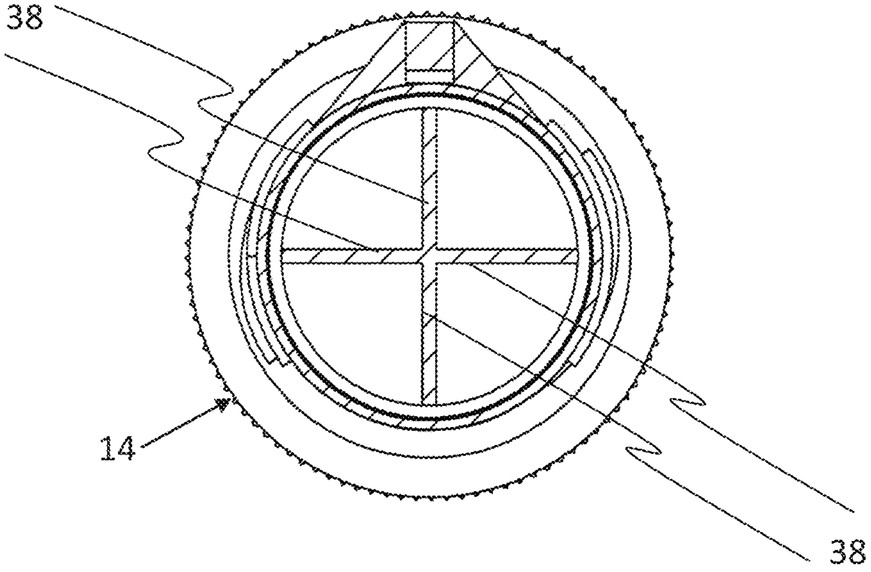
FIG. 6 is a cross section through the line B-B shown in FIG. 1.
Figure 7:
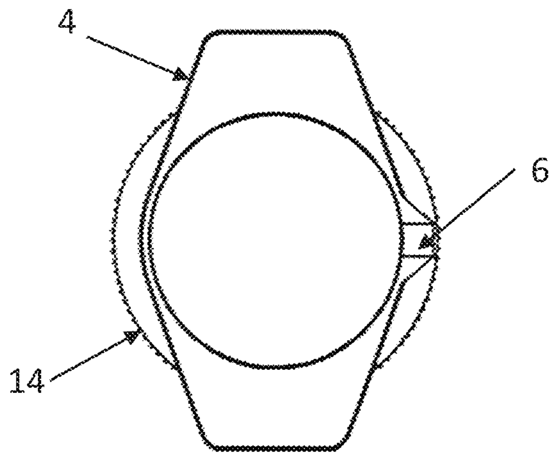
FIG. 7 is a top view of the safety apparatus and the multi-dose syringe as shown in FIG. 1.

The multi-dose syringe 4 is such that the plunger 18 comprises vanes 38. The bottom of the plunger 8 is provided with a rubber seal 40 as shown in FIG. 5. The rubber seal 40 provides sliding sealing contact along the inside of the syringe barrel 6 for injection purposes.

The syringe barrel 6 is provided with an operator squeeze formation 42 in the form of a flange. The two operator squeeze formations 26, 42 are squeezed together in order to cause depression of the plunger 8 along the syringe barrel 6 and thereby effect an injection of a dose of a liquid from the multi-dose syringe 4. The liquid in the multi-dose syringe 4 may be any suitable and appropriate required liquid including drugs such for example as morphine.

The multi-dose syringe 4 has an operating head 44 which is configured for receiving an injection needle (not shown) or a cannula.

The multi-dose syringe 4 may be used for any of the uses for known multi-dose syringes. Thus the multi-dose syringe may be used for injecting a wide variety of drugs for various ailments of human or animal patients.

It is to be appreciated that the embodiments of the invention described above with reference to the accompanying drawings have been given by way of example only and that modifications may be effected. Thus, for example, the body 16, the stopper member 18 and the locating member 22 may be of different constructional shapes to those shown. The dose dial 14 is shown with ribs 46 for facilitating rotation of the dose dial 14. Other gripping formations may be employed. Individual components shown in the drawings are not limited to use in their drawings and they may be used in other drawings and in all aspects of the invention. The invention also extends to the individual components mentioned and/or shown above, taken singly or in any combination.

The invention claimed is:

1. Safety apparatus for a multi-dose syringe, wherein the multi-dose syringe comprises:

(i) a syringe barrel;

(ii) a plunger which operates in the syringe barrel;

(iii) a dose scale on the syringe barrel;

(iv) screw threads on the syringe barrel; and (v) a dose dial which screws along the screw threads for dialling an injection dose on the dose scale;

wherein the safety apparatus comprises:

(vi) a body for extending along the syringe barrel;

(vii) a plunger stopper member which is at a first end portion of the body; and (viii) a locating member which is at a second end portion of the body and which is for locating against the dose dial, wherein the locating member is a wedge formation for becoming wedged in position between the dose dial and the outer side of the syringe barrel;

and wherein the safety apparatus is such that:

(ix) the safety apparatus is securable in position on the multi-dose syringe by screwing the dose dial along the screw threads such that the dose dial tightens against the locating member and thereby causes the plunger stopper member to engage the plunger such as to stop the depression of the plunger into the syringe barrel and thereby to stop injection of a dose from the multi-dose syringe.

2. Safety apparatus according to claim 1 in which the body is an elongate body.

3. Safety apparatus according to claim 2 in which the elongate body is a column.

4. Safety apparatus according to claim 1, in which the plunger stopper member engages the multi-dose syringe by extending underneath an operator squeeze formation on the plunger.

5. Safety apparatus according to claim 1 in which the plunger stopper member extends from the body such as to engage the plunger.

6. Safety apparatus according to claim 1 in which the wedge formation comprises a face portion for engaging with the outer side of the syringe barrel, and a curved portion for engaging with the dose dial.

7. Safety apparatus according to claim 1 and including a guide formation for guiding the safety apparatus during the positioning of the safety apparatus on the syringe barrel.

8. Safety apparatus according to claim 7 in which the guide formation comprises two guide arms which extend from the body at an angle to each other such as to extend around a part of the outer side of the syringe barrel.

* * * * *